United States Patent [19]

van Reeth

[11] Patent Number: 4,933,176

[45] Date of Patent: Jun. 12, 1990

[54] CLEAR SHAMPOO COMPOSITIONS

[75] Inventor: Isabelle M. E. van Reeth, Ecaussines, Belgium

[73] Assignee: Dow Corning Limited, Barry, Wales

[21] Appl. No.: 329,156

[22] Filed: Mar. 27, 1989

[30] Foreign Application Priority Data

Apr. 7, 1988 [GB] United Kingdom ............... 8808157

[51] Int. Cl.$^5$ ........................... A61K 7/06; A61K 7/75
[52] U.S. Cl. ........................................ 424/70; 424/78; 252/DIG. 13; 514/772; 514/788
[58] Field of Search .................... 424/70, 78; 252/DIG. 13; 514/772, 788

[56] References Cited

U.S. PATENT DOCUMENTS

| | | | |
|---|---|---|---|
| 4,001,394 | 1/1977 | Fogel et al. | 424/70 |
| 4,062,939 | 12/1977 | Scott | 424/70 |
| 4,663,159 | 5/1987 | Brode, II et al. | 424/70 |
| 4,678,598 | 7/1987 | Ogino et al. | 424/70 X |
| 4,847,078 | 7/1989 | Sheppard et al. | 424/78 X |

Primary Examiner—Thurman K. Page
Assistant Examiner—Amy Hulina
Attorney, Agent, or Firm—Marc C. Pawl; Sharon K. Severance

[57] ABSTRACT

A shampoo composition comprising from 10 to 60% by weight of (a) one or more anionic surfactants, from 1 to 15% by weight of (b) one or more nonionic surfactants, from 0.1 to 25% by weight of (c) a silicone component, selected from polydiorganosiloxanes and cyclodiorganosiloxanes wherein substantially all organic substituents are lower alkyl groups, from 6 to 18% by weight of (d) a salt of saccharin and from 20 to 70% by weight of (e) water. The saccharin salt is preferably a sodium salt, which acts as optical index adjusting agent to provide a clear shampoo and also renders the foam creamier.

20 Claims, No Drawings

CLEAR SHAMPOO COMPOSITIONS

This invention relates to shampoo compositions and more particularly to optically clear shampoo compositions.

It is desirable to provide shampoo compositions which have beneficial effects on wet and dry hair, for example which improve handle, softness, silkiness and ease of combing of the hair. Such beneficial effects may be obtained by incorporating certain types of silicones into the shampoo compositions. The preferred silicones include polydiorganosiloxanes wherein the organic substituents are alkyl or aryl groups. However, such compounds are not easily incorporated and give rise to opaque or at best translucent shampoo products. It is aesthetically desirable to provide optically clear shampoo compositions.

G.B. Patent Application 2 079 300 discloses a method of formulating an optically clear silicone emulsion which comprises (a) forming a non-transparent silicone oil and water emulsion and (b) adjusting the optical clarity of the emulsion by combining it with an optical index adjusting agent, which is a water soluble polyol or polyether in an amount to render the non-transparent emulsion optically clear.

We have now found that salts of saccharin (benzosulfimide) are particularly useful as optical adjusting agents for shampoo compositions containing silicones.

The invention accordingly provides a shampoo composition comprising from 10 to 60% by weight of (a) one or more anionic surfactants, from 1 to 15% by weight of (b) one or more nonionic surfactants, from 0.1 to 25% by weight of (c) a silicone component, comprising polydiorganosiloxanes or cyclodiorganosiloxanes wherein substantially all organic substituents are lower alkyl groups, from 6 to 18% by weight of (d) a salt of saccharin and from 20 to 70% by weight of (e) water.

The anionic surfactants used in the compositions of the invention, may be any of those surfactants which are acceptable in shampoo compositions. These include for example alkyl sulphates, alkyl ether sulphates, alkaryl sulphonates, alkyl succinates, alkyl sulphosuccinates, N-alkoyl sarcosinates and alpha-olefin sulphonates. The alkyl or alkenyl group has typically 12 to 22 carbon atoms. Examples of suitable anionic surfactants include triethanolamine lauryl sulphate, sodium lauryl sulphate, sodium lauryl ether sulphate and sodium dodecylbenzene sulphonate. It is preferred to use anionic surfactants which have a refractive index with a value in the range of 1.35 to 1.45, most preferably around 1.4, for example triethanolamine lauryl sulphate. Preferably the composition comprises from 10 to 30% most preferably from 15 to 25% by weight anionic surfactants. These surfactants are usually employed for their detergency. Suitable non-ionic surfactants for use in the compositions of the invention include fatty acid alkanolamides, alkylene oxide condensates of long chain fatty alcohols, alkylene oxide condensates of alkylphenols and polyorganosiloxane polyoxyalkylene copolymers. Examples of such surfactants include coconut diethanolamide, lauric diethanolamide, ethylene oxide condensates of mirystyl alcohol and octylphenol-8 mole ethylene oxide condensates. Preferably the nonionic surfactants used also have a refractive index value in the range from 1.35 to 1.48, most preferably about 1.40. Preferably the composition comprises from 1 to 10% by weight of a non-ionic surfactant, most preferably from 3 to 8%. The nonionic surfactant is believed to aid the emulsification of water insolubale materials. It also tends to improve the quality of the shampoo foam, especially in respect of its creaminess.

The silicone component of the composition comprises polydiorganosiloxanes or cyclodiorganosiloxanes wherein substantially all organic substituents are lower alkyl groups. These are polysiloxanes of the general formula $R_3Si(OSiR_2)_nR$ and $(R_2SiO)_m$ respectively, wherein R represents a lower alkyl group, n represents a value of at least 1 and m represents a value of from 3 to about 18. Although linear and cyclic diorganosiloxanes are preferred, a small amount of branching may be present in the molecules. Preferably all R groups are methyl, but a small number of alkyl groups having from 2 to 6 carbon atoms, hydroxyl groups or phenyl groups may be present on the polysiloxane. Preferably the silicone component consists only of dimethicone, cyclomethicone or a mixture of both. The refractive index of these silicone materials is approximately 1.4. Polydiorganosiloxanes suitable for use in the compositions of the invention, may have a viscosity which ranges from $0.65$ mm$^2$/s to more than 1 m$^2$/s. The use of higher viscosity diorganosiloxanes may be facilitated by mixing with, e.g. cyclic diorganosiloxanes or other low viscosity silicone compounds. The most preferred silicone component comprises dimethicone having a viscosity of about 350 mm$^2$/s. The use of the preferred silicone component results in more desirable properties such as ease of combing, ease of disentanglement and a silky feeling (i.e. good handle) being imparted to the hair. Up to 25% by weight of silicone component may be used in the composition. Preferably from 1 to 10% is used, and most preferably from 2 to 7%.

The salt of saccharin is used as an optical index adjusting agent, rendering the composition optically clear. Preferably the sodium salt is used. The amount of Na saccharin which may be used varies according to the refractive index of the water solubale parts of the composition. At least 6% by weight is required in order to obtain an optically clear shampoo composition. As the saccharin salt is water soluble, the greater the proportion of water present the higher the proportion of the salt that can be added and therefore the greater the difference in refractive index between the water insoluble and the water soluble part of the composition which may be overcome. The maximum level which may be used is 18% by weight. Higher levels cause the viscosity of the composition to rise above acceptable levels. Preferably between 6 and 10% of saccharin salt is used.

The compositions of the invention may also contain a number of optional ingredients. These include organic cationic conditioning agents, for example quaternary ammonium compounds, aminofunctional silicone conditioning agents, amphoteric surfactants, perfume, colouring, dye, preservative, thickeners, for example cellulosic thickeners but preferably polyethylene glycol-120 methyl glucose dioleate, and NaCl, which is used to increase the viscosity of the composition. The amount of optional components does not usually exceed 15% by weight of the total composition.

The composition may be prepared by simply mixing all ingredients together, and stirring them thoroughly. Heat may be applied to improve the dispersion of the ingredients. It is not necessary to form an emulsion of some or all of the silicone component prior to incorporating the saccharin salt. This helps to keep the cost of manufacturing down.

According to another aspect of the invention there is provided a method of making clear shampoo compositions comprising mixing together (a) from 10 to 60% by weight of one or more anionic surfactants, (b) from 1 to 15% by weight of one or more nonionic surfactants, (c) from 0.1 to 25% by weight of a silicone component, comprising polydiorganosiloxanes or cyclodiorganosiloxanes wherein substantially all organic substituents are lower alkyl groups, (d) from 6 to 18% by weight of a salt of saccharin and (e) from 20 to 70% by weight of water.

It was found that shampoo compositions according to the invention impart improved effects to hair. It is believed that the use of Na saccharin as index adjusting agent has particularly beneficial effects. The foam quality of the shampoo in use was found to be much superior to the quality of foam obtained by a shampoo which did not contain a saccharin salt. The foam was more creamy. It is also believed that the use of saccharin salt improved the handle and the dry combing of hair which had been washed with a shampoo composition according to the invention.

The invention accordingly also provides a method of treating hair which comprises washing the hair with a shampoo composition according to the first aspect of the invention.

The following examples, in which all parts and percentages are expressed by weight, illustrates the invention.

EXAMPLE 1

45 parts of Empicol TL40/T (triethanolamine lauryl sulphate, provided by the Marchon Division of Albright and Wilson), 6 parts of Empilan CDE (ethanolamides of coconut acid, provided by the Marchon Division of Albright and Wilson), 7 parts of Na saccharin, 5 parts of NaCl, 5 parts of Glucamate DOE 120 (polyethylene glycol-120 methyl glucose dioleate, provided by Amerchol), 5 parts of a polydimethylsiloxane having a viscosity of 350 mm$^2$/s, 0.48 part ascorbic acid and water up to 100 parts, were mixed together while heating, until a clear homogeneous liquid was obtained having a viscosity of $1.8 \times 10^3$ mm$^2$/s and a pH of 6.62.

EXAMPLE 2

A shampoo composition was prepared as in Example 1, except that 0.48 part of ascorbic acid were replaced by 0.3 part of citric acid. The viscosity was $2 \times 10^3$ mm$^2$/s and the pH 6.73.

EXAMPLE 3

A shampoo composition was prepared as in Example 2, except that 5 parts of a polydimethylsiloxane having a viscosity of 350 mm$^2$/s were replaced with 3 parts of a mixture of 13% of a very high viscosity polydimethyl siloxane having terminal dimethyl hydroxy silyl groups in cyclomethicone. A composition with a viscosity of $36.5 \times 10^3$ mm$^2$/s was obtained with a pH of 6.94.

EXAMPLE 4

A shampoo composition was prepared by mixing together 45 parts of Empicol TL40/T, 8 parts of Empilan CDE, 2 parts of a polydimethylsiloxane having a viscosity of 350 mm$^2$/s, 14 parts of Na saccharin, and water up to 100 parts. The mixture was heated and a clear shampoo composition was obtained.

EXAMPLE 5

A shampoo composition was prepared as in Example 4, except that only 7 parts of Na saccharin was used and 7 parts of Na ascorbate were added. A clear shampoo composition was obtained.

EXAMPLE 6

A shampoo composition was prepared as in Example 4, except that 9 parts of Na saccharin were used and 5 parts of NaCl were added. A clear shampoo composition was obtained.

EXAMPLES 7–11

Shampoo compositions were prepared as in Example 6, except that 2 parts of a polydimethylsiloxane having a viscosity of 350 mm$^2$/s were replaced in Example 7 with 5 parts of a polydimethylsiloxane having a viscosity of 350 mm$^2$/s, in Example 8 with 4 parts of a polydimethylsiloxane having a viscosity of $1 \times 10^3$ mm$^2$/s, in Example 9 with 6 parts of a polydimethylsiloxane having a viscosity of $1.25 \times 10^4$ mm$^2$/s, in Example 10 with 6 parts of a polydimethylsiloxane having a viscosity of $6 \times 10^4$ mm$^2$/s and in Example 11 with 3 parts of a mixture of 13% of a very high viscosity polydimethyl siloxane having terminal dimethyl hydroxy silyl groups in cyclomethicone.

All of the compositions were optically clear.

EXAMPLE 12

The Example shampoo compositions 4 to 11 were tested for their ability to ease the combing of hair, both when wet after shampooing, and when dry, for their ability to reduce static, and for the handle (feel and body) they impart to the hair. The tests were carried out as follows.

A hair swatch (European natural brown hair), was wetted and washed with the Example shampoo. The hair swatch was rinsed well in running water. When the excess of water had been removed, the hair swatch was tested for wet combability. This was done by passing a fine plastic comb through the hair and assessing the ease of combing. The hair swatch was then dried during one hour in an air-circulating oven at 70° C. When the hair was cooled to room temperature dry combability was assessed. The handle was assessed by feeling the hair and considering its softness, silkiness and body. This test is usually carried out by a panel of experienced people. The static of the hair was assessed by combing the dry hair five times downwards with a plastic comb, and comparing the angle at which the hair spreads out before and after the combing. All test results are shown in Tables I and II, wherein different shampoo compositions were compared with each other, and comparative ratings were given for each tested effect (lower values indicating better results). In Table I a comparative test was done, by using a Control shampoo composition consisting of 20 parts Empicol ESB 70 (sodium salt of sulphated ethoxylated lauryl alcohol, 68% in water, provided by the Marchon division of Albright and Wilson), 5.5 parts of Empicol 0627 (a concentrated blend of anionic and nonionic components, provided by the Marchon division of Albright and Wilson), 3.5 parts of Empilan 2125 (linoleic diethanolamide, provided by the Marchon division of Albright and Wilson), qs of NaCl and of citric acid, and water up to 100 parts.

TABLE I

| Example Composition | Wet Combing | Dry Combing | Handle | Static |
|---|---|---|---|---|
| 4 | — | 1 | 1 | 1 |
| 5 | — | 2 | 2 | 1 |
| Control | — | 3 | 3 | 3 |

Table II shows a comparison between the Compositions of Examples 7 to 11, the Control composition of Table I and two commercially available clear shampoo compositions X and Y. Composition X is known to contain water, ammonium lauryl sulphate, ammonium laureth sulphate, dimethicone, ammonium xylene sulphonate, glycol distearate, fragrance, cocamide DEA, tricetylammonium chloride, xantham gum, cetyl alcohol, methylchloroisothiazoline, methylisothiazolinone, Na citrate and citric acid. Composition Y is known to contain water, corn syrup, triethanolamine lauryl sulphate, SD alcohol 40, cocamide MEA, triethanolamine, dimethicone, hydroxypropyl methylcellulose, fragrance, guar hydroxypropyl trimonium chloride, Na hydroxymethane sulphonate and EDTA.

TABLE II

| Example Composition | Wet Combing | Dry Combing | Handle | Static |
|---|---|---|---|---|
| Control | 8 | 8 | 8 | 8 |
| X | 1 | 1 | 1 | 3 |
| Y | 6 | 7 | 5 | 2 |
| 7 | 3 | 3 | 1 | 3 |
| 8 | 3 | 4 | 7 | 3 |
| 9 | 1 | 6 | 6 | 3 |
| 10 | 3 | 5 | 1 | 3 |
| 11 | 6 | 2 | 4 | 1 |

These results indicate that the use of Na saccharin, especially in combination with a polydimethylsiloxane having a viscosity of 350 mm$^2$/s performs very well in a shampoo. The foam itself was also studied, and was found to be much creamier than the foam of the control shampoo composition.

That which is claimed is:

1. A shampoo composition comprising from 10 to 60% by weight of (a) one or more anionic surfactants, from 1 to 15% by weight of (b) one or more nonionic surfactants, from 0.1 to 25% by weight of (c) a silicone component, selected from polydiorganosiloxanes and cyclodiorganosiloxanes wherein substantially all organic substituents are lower alkyl groups, from 6 to 18% by weight of (d) a salt of saccharin and from 20 to 70% by weight of (e) water.

2. A shampoo composition according to claim 1 comprising from 10 to 30% by weight of (a).

3. A shampoo composition according to claim 2, comprising from 15 to 20% by weight of (a).

4. A shampoo composition according to claim 1, comprising from 1 to 10% weight of (b).

5. A shampoo composition according to claim 4, comprising from 3 to 8% by weight of (b).

6. A shampoo composition according to claim 1, wherein the refractive index of the anionic surfactants has a value in the range of 1.35 to 1.48.

7. A shampoos composition according to claim 1, wherein the refractive index of the nonionic surfactants has a value in the range of 1.35 to 1.48.

8. A shampoo composition according to claim 6, wherein the refractive index of the anionic surfactants has a value of about 1.40.

9. A shampoo composition according to claim 7, wherein the refractive index of the nonionic surfactants has a value of about 1.40.

10. A shampoo composition according to claim 1, comprising from 1 to 10% by weight of (c).

11. A shampoo composition according to claim 10, comprising from 2 to 7% by weight of (c).

12. A shampoo composition according to claim 1, wherein substantially all organic groups of the silicone component are methyl groups.

13. A shampoo composition according to claim 1, wherein (c) comprises a dimethicone having a viscosity at 25° C. of 350 mm$^2$/s.

14. A shampoo composition according to claim 1, comprising from 6 to 10% by weight of (d).

15. A shampoo composition according to claim 1, wherein (d) is a sodium salt of saccharin.

16. A shampoo composition according to claim 1, comprising from 15 to 25% by weight of (a), from 3 to 8% by weight of (b), from 2 to 7% by weight of (c) and from 6 to 10% by weight of (d).

17. A shampoo composition according to claim 16, wherein the refractive index of the anionic and the nonionic surfactants has a value in the range of 1.35 to 1.48.

18. A shampoo composition according to claim 16, wherein (c) comprises a dimethicone having a viscosity at 25° C. of 350 mm$^2$/s and (d) is a sodium salt of saccharin.

19. A method of making clear shampoo compositions comprising mixing together (a) from 10 to 60% by weight of one or more anionic surfactants, (b) from 1 to 15% by weight of one or more nonionic surfactants, (c) from 0.1 to 25% by weight of a silicone component, selected from polydiorganosiloxanes and cyclodiorganosiloxanes wherein substantially all organic substituents are lower alkyl groups, (d) from 6 to 18% by weight of a salt of saccharin and (e) from 20 to 70% by weight of water.

20. A method of treating hair which comprises washing the hair with a shampoo composition according to claim 1.

* * * * *